(12) United States Patent
Delrot et al.

(10) Patent No.: US 11,155,774 B2
(45) Date of Patent: Oct. 26, 2021

(54) METHOD AND APPARATUS FOR GENERATING THREE-DIMENSIONAL PATTERNED SOFT STRUCTURES AND USES THEREOF

(71) Applicant: ECOLE POLYTECHNIQUE FEDERALE DE LAUSANNE (EPFL), Lausanne (CH)

(72) Inventors: Paul Delrot, Morges (CH); Sylvain Paul Hauser, Moutier (CH); Jan Krizek, Lausanne (CH); Christophe Moser, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 700 days.

(21) Appl. No.: 16/018,226

(22) Filed: Jun. 26, 2018

(65) Prior Publication Data

US 2018/0371389 A1 Dec. 27, 2018

(30) Foreign Application Priority Data

Jun. 27, 2017 (WO) .................. PCT/IB2017/053831

(51) Int. Cl.
*B33Y 10/00* (2015.01)
*C12M 3/00* (2006.01)
(Continued)

(52) U.S. Cl.
CPC .......... *C12M 21/08* (2013.01); *B29C 64/112* (2017.08); *B33Y 10/00* (2014.12); *B33Y 30/00* (2014.12);
(Continued)

(58) Field of Classification Search
CPC ..... C12M 21/08; C12M 33/00; B29C 64/112; B33Y 10/00; B33Y 70/00; B33Y 30/00;
(Continued)

(56) References Cited

U.S. PATENT DOCUMENTS 7,014,885 B1 3/2006 Piqué et al.
9,248,684 B2 * 2/2016 Wang ....................... B41M 5/52
(Continued)

OTHER PUBLICATIONS

Guillotin, B., Souquet, A., Catros, S., Duocastella, M., Pippenger, B., Bellance, S., . . . & Guillemot, F. (2010). Laser assisted bioprinting of engineered tissue with high cell density and microscale organization. Biomaterials, 31(28), 7250-7256.
(Continued)

*Primary Examiner* — Rick K Chang
(74) *Attorney, Agent, or Firm* — Andre Roland S.A.; Nikolaus Schibli

(57) ABSTRACT

A method for generating a three-dimensional patterned soft structure, including the steps of providing a soft supporting substrate, providing a drop-on-demand system with a device for varying the velocity of the jetted droplets, providing a liquid ink, jetting the liquid ink towards the soft supporting substrate with the drop-on-demand system, controlling an injection depth of the liquid ink into the soft supporting substrate by varying a jetting velocity of the liquid ink; and depositing droplets of the liquid ink over a volume of the soft supporting substrate, thereby generating the three-dimensional patterned soft structure.

20 Claims, 6 Drawing Sheets

(51) Int. Cl.
 B33Y 70/00 (2020.01)
 C12N 5/00 (2006.01)
 B33Y 30/00 (2015.01)
 B29C 64/112 (2017.01)
 B33Y 80/00 (2015.01)
 B29L 31/00 (2006.01)
 C12M 1/26 (2006.01)

(52) U.S. Cl.
 CPC ............ *B33Y 70/00* (2014.12); *C12N 5/0062* (2013.01); *B29L 2031/7532* (2013.01); *B33Y 80/00* (2014.12); *C12M 33/00* (2013.01)

(58) Field of Classification Search
 CPC ............... B33Y 80/00; C12N 5/0062; B29L 2031/7532
 See application file for complete search history.

(56) References Cited

U.S. PATENT DOCUMENTS

| | | |
|---|---|---|
| 2004/0137710 A1 | 7/2004 | Grigoropoulos et al. |
| 2017/0028626 A1 | 2/2017 | Delrot et al. |

OTHER PUBLICATIONS

Hinton, T. J., Jallerat, Q., Palchesko, R. N., Park, J. H., Grodzicki, M. S., Shue, H. J., . . . & Feinberg, A. W. (2015). Three-dimensional printing of complex biological structures by freeform reversible embedding of suspended hydrogels. Science advances, 1(9), e1500758.

Pataky, K., Braschler, T., Negro, A., Renaud, P., Lutolf, M. P., & Brugger, J. (2012). Microdrop Printing of Hydrogel Bioinks into 3D Tissue-Like Geometries. Advanced Materials, 24(3), 391-396.

Brown, Matthew S., Nicholas T. Kattamis, and Craig B. Arnold. "Time-resolved study of polyimide absorption layers for blister-actuated laser-induced forward transfer." Journal of Applied Physics 107.8 (2010): 083103.

Chen, Alvin U., and Osman A. Basaran. "A new method for significantly reducing drop radius without reducing nozzle radius in drop-on-demand drop production." Physics of fluids 14 (2002): L1-L4.

Duocastella, M., et al. "Film-free laser forward printing of transparent and weakly absorbing liquids." Optics express 18.21 (2010): 21815-21825.

Guillemot, F., et al. "High-throughput laser printing of cells and biomaterials for tissue engineering." Acta biomaterialia 6.7 (2010): 2494-2500.

Murphy, Sean V., and Anthony Atala. "3D bioprinting of tissues and organs." Nature biotechnology 32.8 (2014): 773-785.

Papadopoulos, Ioannis N., et al. "Focusing and scanning light through a multimode optical fiber using digital phase conjugation." Optics express 20.10 (2012): 10583-10590.

Reis, N., and B. Derby. "Ink jet deposition of ceramic suspensions: Modeling and experiments of droplet formation." MRS proceedings. vol. 625. Cambridge University Press, 2000.

Shin, Jason Y., and Nicholas L. Abbott. "Using light to control dynamic surface tensions of aqueous solutions of water soluble surfactants." Langmuir 15.13 (1999): 4404-4410.

Tagawa, Yoshiyuki, et al. "Highly focused supersonic microjets." Physical review X 2.3 (2012): 031002.

Tagawa, Yoshiyuki, et al. "Needle-free injection into skin and soft matter with highly focused microjets." Lab on a Chip 13.7 (2013): 1357-1363.

\* cited by examiner

METHOD AND APPARATUS FOR GENERATING THREE-DIMENSIONAL PATTERNED SOFT STRUCTURES AND USES THEREOF

CROSS REFERENCE TO RELATED APPLICATIONS

The present invention claims foreign priority to International patent application PCT/IB2017/053831 filed on Jun. 27, 2017, the entire contents thereof herewith being incorporated by reference.

FIELD OF THE INVENTION

The present invention relates to methods of generating three-dimensional patterned soft structures, on which cells may be seeded. In particular, the present invention relates to printing systems wherein droplets of soft materials are generated and deposited into a soft substrate to form three-dimensional structures.

BACKGROUND

Three-dimensional printing technologies for biomedical applications have received considerable interest in the recent years as they speed up innovations in tissue generation for transplantation or drug discovery. The replication of tissues and organs with suitable mechanical and functional properties requires reproducing the complex micro-architecture of cells and extracellular components that can be found in living organisms.

Three main techniques are used for deposition of biological material, namely inkjet printing, micro-extrusion and laser-induced forward transfer (LIFT). All these techniques suffer from a slow printing speed when it comes to printing biological liquid suspensions. Despite the use of advanced crosslinking strategies. See for example in Pataky et al., "Microdrop Printing of Hydrogel Bioinks into 3D Tissue-Like Geometries," Adv. Mater., Vol. 24, No. 3, pp. 391-396, January 2012, building a three-dimensional structure with a liquid ink indeed requires to wait for the volume of the basis layer to solidify before printing a fresh layer of ink on top of it, thus limiting the printing speed of a single layer.

Similarly, the use of liquid inks is detrimental to the printing resolution since the spreading time of liquid inks is significantly faster than their crosslinking time. Furthermore, some soft structures collapse during printing owing to their poor mechanical properties. Using a support material for the printed soft structure can solve the two latest issues by first maintaining the shape of the volume of liquid ink while it crosslinks, and second by providing a stiff frame for the soft printed structure, thus retaining the structural integrity of the printed part.

Recently, it has been demonstrated that Bingham plastics materials can be used as a good support frame for three-dimensional soft-structures. Hinton et al., "Three-Dimensional Printing of Complex Biological Structures by Freeform Reversible Embedding of Suspended Hydrogels," Sci Adv, Vol. 1, No. 9, September 2015. Bingham plastics, such as gelatin, exhibit a solid behavior at low shear stress but act as liquids at higher shear stresses. In this way, a soft structure, which was gently extruded out of a nozzle, was held in place into gelatin, whereas the thin nozzle could still move freely into the supporting bath of gelatin.

Despite the recent advancements in the field of generating three-dimensional patterned soft structures, still further improvements of the printing techniques are desired, to improve soft three-dimensionally printed structures.

SUMMARY OF THE INVENTION

According to one aspect of the present invention, a physical mechanism and device structure is presented that allows for the generation of three-dimensional patterned soft structures with micro-scale control. The methods described herein provide an additional degree of control of the deposition of soft material than methods previously described thus resulting in a faster printing throughput, a finer axial printing resolution and the ability to print more complex soft structures than the background art.

According to another aspect of the present invention, a method for controlling the deposition depth of small volumes of a soft material ink into a supporting soft substrate is provided. Accordingly, within an aspect of the present invention, a volume of soft substrate that is used as a support material for the printed soft structure. The volume of the soft substrate can have, but not limited to, a flat top interface with air. The height of the volume of soft substrate can be, but not limited to, 300 μm to 1000 μm. In at least one embodiment, the substrate has rheological properties similar to that of a Bingham plastic, behaving as a solid body under a threshold shear stress but acting as a viscous liquid at higher shear stresses, but not limited to. The soft substrate can be, but not limited to, gelatin.

According to another aspect of the present invention, a system for generating a three-dimensional patterned soft structure by using a soft supporting substrate is provided. The system preferably includes a light source for generating a light beam, a device for controlling an intensity of the light beam of the light source to generate a controlled light beam, an ink jetting layer having a liquid layer of ink, a solid-state light absorbing film, and a transparent solid layer, the controlled light beam impinging on the solid-state light absorbing film to generate a droplet from the liquid layer of ink, a stage for moving the controlled light beam relative to the ink jetting layer, and a soft supporting substrate for receiving the droplet at different depths as a function of the intensity of the light beam.

According to yet another aspect of the present invention, a method for generating a three-dimensional patterned soft structure is provided, by using a soft supporting substrate, a drop-on-demand system with a device for varying the velocity of jetted droplets, and a liquid ink. Preferably the method includes the steps of jetting the liquid ink towards the soft supporting substrate with the drop-on-demand system, controlling an injection depth of the liquid ink into the soft supporting substrate by varying a jetting velocity of the liquid ink, and depositing droplets of the liquid ink over a volume of the soft supporting substrate to generate the three-dimensional patterned soft structure.

According to some aspects, the method uses a drop-on-demand delivery system that generates droplets or jets of the soft material ink with a velocity range of 10 meters per second to 200 meters per second, but not limited to this range. When the velocity of the droplets of the soft material ink is high enough at the impact on the soft substrate interface, the induced shear stress exceeds the yield stress of the soft substrate and the soft material ink will penetrate and flow into the soft substrate. When the viscous drag of the soft substrate eventually slows down the small volume of soft material ink below a threshold velocity, the induced shear stress on the soft substrate is inferior to the soft substrate yield stress. Consequently, the droplet of soft material ink eventually stops and the soft substrate acts as a solid thus supporting the small volume of deposited ink.

According to yet another aspect, the method includes the control of the initial jetting velocity and the volume of the soft material ink ejected. This allows for varying the depth at which the small volume of soft material ink will be deposited into the soft substrate. Higher velocity of the small volume of soft material ink indeed results in longer paths of the droplet into the soft substrate before the viscous drag of the soft substrate eventually stops the droplet of soft material ink.

In at least one embodiment, small volumes of the soft material ink are deposited serially or in parallel at different depths and over a large surface into the soft substrate, thus forming three-dimensional pattern of the soft material ink into the soft substrate.

The methods may use a crosslinking mechanism of the soft material ink. In at least one embodiment, the soft substrate volume may act as a reservoir for a crosslinking component of the soft material ink. The soft material ink can be, but not limited to, alginate. The soft substrate can contain, but not limited to, divalent cations such as $Ca^{2+}$.

The methods may comprise a step of seeding cells or biological content in the soft material ink and therefore in the patterned soft structure.

In at least one embodiment, the drop-on-demand system includes a solid transparent substrate that can be, but not limited to, silica glass. In at least one embodiment, a thin solid-state light-absorbing film is coated on the solid transparent substrate and a thin layer of the soft material ink is coated on top of the light-absorbing film. A single spot or several spots of a light pulses are focused simultaneously or serially onto the light-absorbing film. When the energy delivered into a light spot is high enough, a transient bubble and a shockwave are generated. The consequent shockwave leads to the generation of a droplet or a jet of the soft material ink. The velocity of the generated droplet can be controlled as it increases with absorbed the light pulse energy. The thin soft material ink layer can be 10 µm to 60 µm, but not limited to. The light can be, but not limited to, laser light. The laser pulse width can be, but not limited to 5 ns to 2 µs. The laser pulse energy can be, but not limited to 0.5 µJ-300 µJ. The thickness of the light-absorbing layer can be, but not limited to 10 nm-10 µm. The solid-state light-absorbing film can be, but not limited to, a metal or a polymer. The solid-state light-absorbing film can be, but not limited to gold or platinum. In at least one embodiment, the solid-state light-absorbing film is a polymer, such as Kapton® polyimide, but not limited to.

In at least one embodiment, the light beam focused onto the light-absorbing film is spatially shaped to control the ejection of the biological material suspended in the liquid ink. For example, the light beam is shaped as a doughnut beam, but not limited to, and can be used to constrain a cell to be contained in the generated liquid droplet by inducing a flow focusing effect.

In at least one embodiment, the drop-on-demand system include one or several inkjet printer heads that are used to generate droplets of varying velocities.

Furthermore, in at least one embodiment, the present invention relates to biological three-dimensional printing of human or animal skin model.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

Herein, identical reference numerals are used, where possible, to designate identical elements that are common to the figures. Also, the images are simplified for illustration purposes and may not be depicted to scale.

DETAILED DESCRIPTION OF THE SEVERAL EMBODIMENTS

According to one aspect of the present invention, a method is provided for generating three-dimensional patterned soft structures, into which cells may be seeded, as well as methods of using theses structures. In particular, according to another aspect of the present invention, a method is provided for controlling the axial deposition of soft materials by adjusting the injection velocity of the soft materials into a soft substrate.

The techniques, apparatus, materials and systems as described in this specification can be used to implement a printing system of three-dimensional patterned soft structures.

Figure 1:
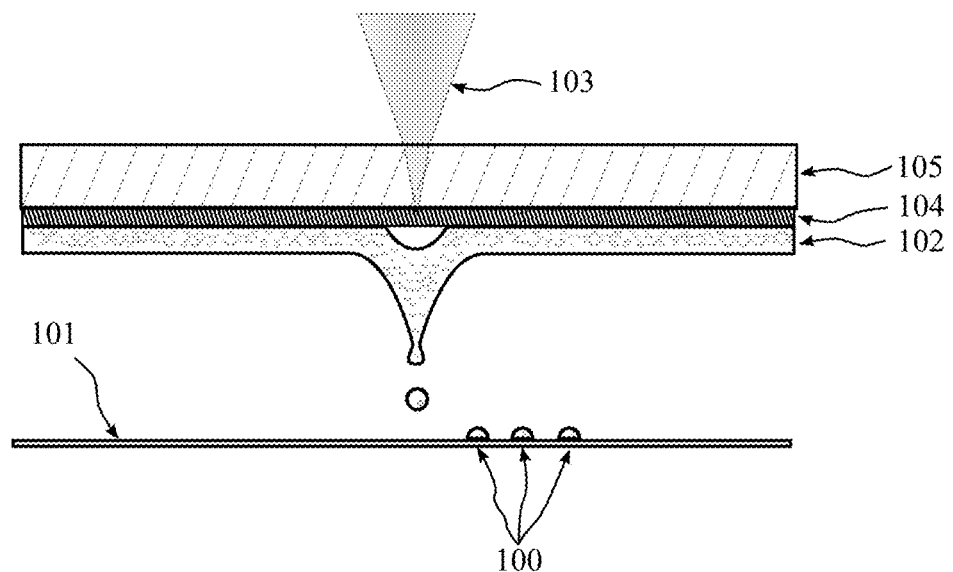
FIG. 1 shows an exemplary cross-sectional drawing of an example of a background art device that is limited to two-dimensional patterning of soft ink. Droplets 100 of the soft ink are deposited on a solid or soft substrate 101 without controlling their deposition depth. Droplets 100 are generated from a thin liquid layer of ink 102 by focusing a laser beam 103 onto a thin solid-state light-absorbing film 104 coated onto a transparent solid substrate 105. This background art device for laser-actuated printing that can only achieve two-dimensional patterning of soft ink.
Figure 2:
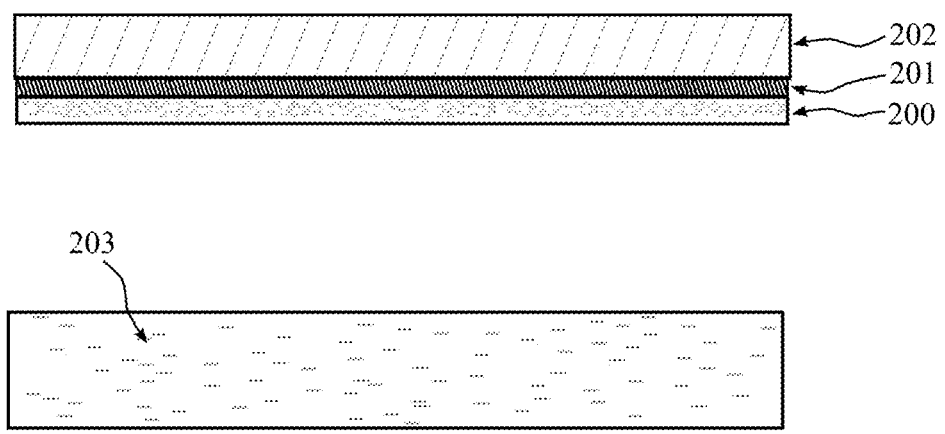
FIG. 2 shows an exemplary cross-sectional drawing of an embodiment of the soft-structures printing apparatus showing a drop-on-demand system comprised of thin liquid ink layer 200 coated on a thin solid-state light-absorbing layer 201, which is itself coated on a transparent solid material 202. A large volume of a soft supporting substrate 203 is placed below the drop-on-demand system. This depicts an embodiment of the system with a light-actuated drop-on-demand delivery, before actuation.
Figure 3:
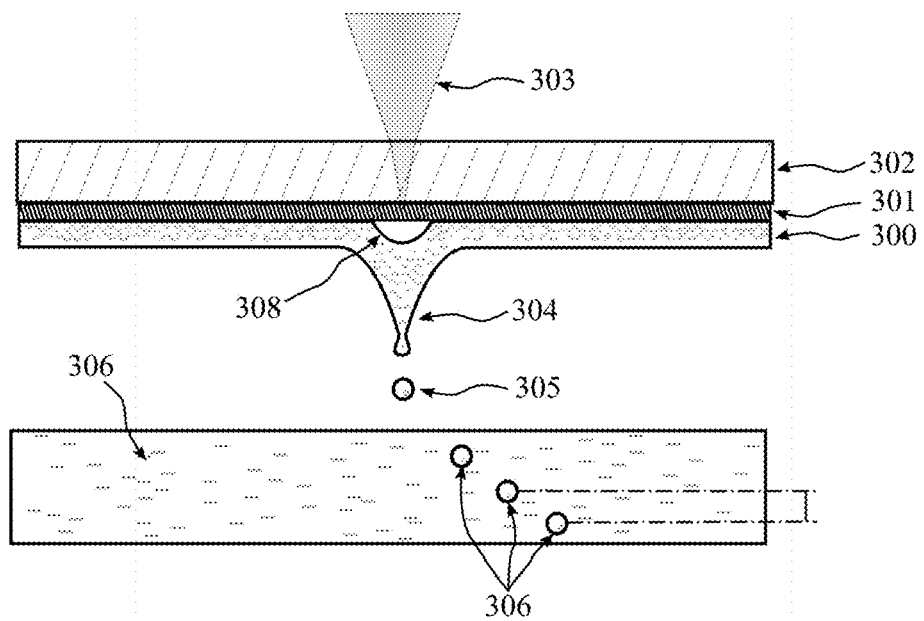
FIG. 3 shows an exemplary cross-sectional drawing of an embodiment of the soft-structures printing apparatus showing the laser-actuated delivery of a liquid ink towards a soft substrate. 300 corresponds to the liquid layer of the ink to dispense coated onto a thin solid-state light-absorbing film 301, which is itself coated on a transparent solid material 302. A light pulse 303 is focused onto the light-absorbing film 301, hence vaporizing part of the film 301 and the liquid 300 and leading to the generation of a high-velocity liquid jet 304 and the delivery of a subsequent droplet 305 into a soft supporting substrate 306. 307 corresponds to droplets deposited at different depths into the substrate 306. 308 corresponds to the transient bubble generated by the light pulse. This is an embodiment of the system with a light-actuated drop-on-demand delivery, after actuation.

Described is a three-dimensional printing system of patterned soft structures composed of at least a drop-on-demand delivery system and a soft support material. FIG. 1 shows a background art laser-actuated printing device. This device does not allow to control the deposition depth of liquid inks into a substrate and therefore can only achieve two dimensional patterning. FIGS. 2 and 3 show a depiction of a cross-section of an embodiment of the system. The drop-on-demand system is composed of a light-transparent solid-state substrate onto which a thin solid-state light-absorbing film is coated. A thin layer of the liquid ink is coated onto the light-absorbing film. The liquid ink can be, but not limited to, a mixture of water, glycerin and alginate seeded with cells or a biological suspension. The liquid ink can be coated, for example, with a doctor blade. The light-absorbing film can be, but not limited to, made of metal or polymer, and deposited by, for instance, sputtering and spin coating respectively. The light-transparent substrate can be, but not limited to, silica glass. The soft substrate is a volume of a material that can have, but not limited to, similar rheological properties as Bingham plastics. The soft substrate can be stored in a solid transparent container in order to facilitate imaging of the printed structure. The soft substrate can include, but not limited to, gelatin.

According to one aspect, it is proposed to take advantage of the rheological properties of Bingham plastics to extend the conventional printing range of jetting methods, such as LIFT and inkjet printing, from sequential two-dimensional patterning to build a three-dimensional pattern, to direct three-dimensional patterning of soft structures. With this aim in mind, the deposition depth of a droplet into a soft Bingham plastic substrate is controlled by varying its initial jetting velocity from the drop-on-demand system. When the velocity of the droplets of the liquid ink is high enough at the impact on the substrate interface, the induced shear stress exceeds the yield stress of the soft substrate and the soft material ink will penetrate and flow into the soft substrate until the viscous drag of the soft substrate eventually slows it down. Under a threshold velocity, the induced shear stress on the soft substrate is inferior to the soft substrate yield stress. Consequently, the droplet of soft material ink eventually stops and the soft substrate acts as a solid, thus supporting the small volume of deposited ink.

For instance, in LIFT of liquids, an infrared or ultraviolet nanosecond laser pulse is focused on a thin light-absorbing film to produce a shockwave and transfer a small volume of ink to a soft receiving substrate. See for example U.S. Pat. No. 7,014,885, this reference herewith incorporated by reference in its entirety. This method does not allow to control the deposition depth of the ink into the receiving substrate. See for example Guillotin et al., "Laser Assisted Bioprinting of Engineered Tissue with High Cell Density and Microscale Organization," Biomaterials, Vol. 31, No. 28, September 2010. By varying the laser pulse energy here it is proposed to control the jetting velocity of the ink and therefore directly target a specified depth into a thick soft supporting volume, hence adding a degree of freedom to this jetting method.

Figure 4:
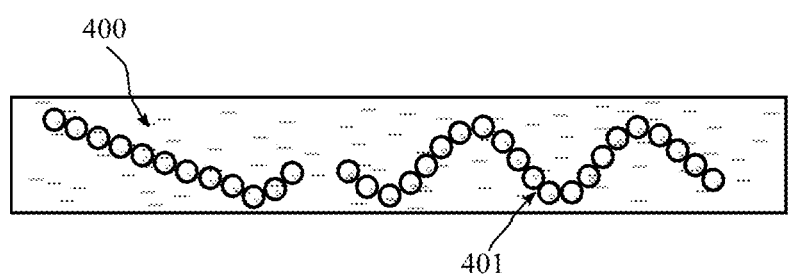
FIG. 4 shows an exemplary cross-sectional drawing of the soft substrate 400 into which three-dimensional patterns 401 of a soft ink have been printed with the device of shown in FIG. 2, being an example of three-dimensional patterned soft structure directly printed into a soft substrate.

FIG. 2 shows a laser light pulse focused onto the thin solid-state light-absorbing film. When the light pulse energy is high enough, the heat generated on the light-absorbing film suddenly vaporizes a small volume of liquid, hence generating a bubble and a shockwave. If the consequent kinetic energy imparted to the liquid ink layer is large enough, a thin jet and/or a droplet is generated. If the velocity of the droplet is large enough to induce a shear stress exceeding the yield stress of the soft substrate, the droplet flows into the substrate until it eventually stops owing to the viscous drag of the soft substrate. The soft substrate then supports the deposited droplet. By varying the laser energy and therefore the droplet jetting velocity, droplets of the ink can be deposited at different depths as shown in FIG. 3. Higher laser energy results in larger jetting velocity and deeper deposition of droplets into the substrate. A three-dimensional soft structure is eventually printed by depositing droplets over the whole surface of the soft substrate, as described in FIG. 4.

Figure 5:
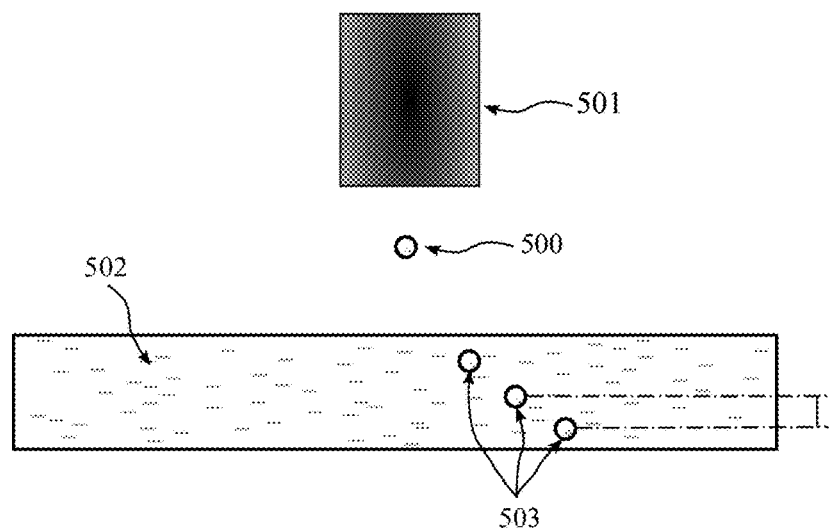
FIG. 5 shows an exemplary cross-sectional drawing of an embodiment of the soft-structures printing apparatus having a printer head 501, showing a liquid droplet 500 ejected from a printer head 501 towards a soft substrate 502. 503 corresponds to droplets deposited at different depths into the substrate 502.

In at least one embodiment, the drop-on-demand system can be an inkjet printer head as described in FIG. 5. The control over the deposition depth of the ink is also ensured by varying the jetting velocity.

Figure 6:
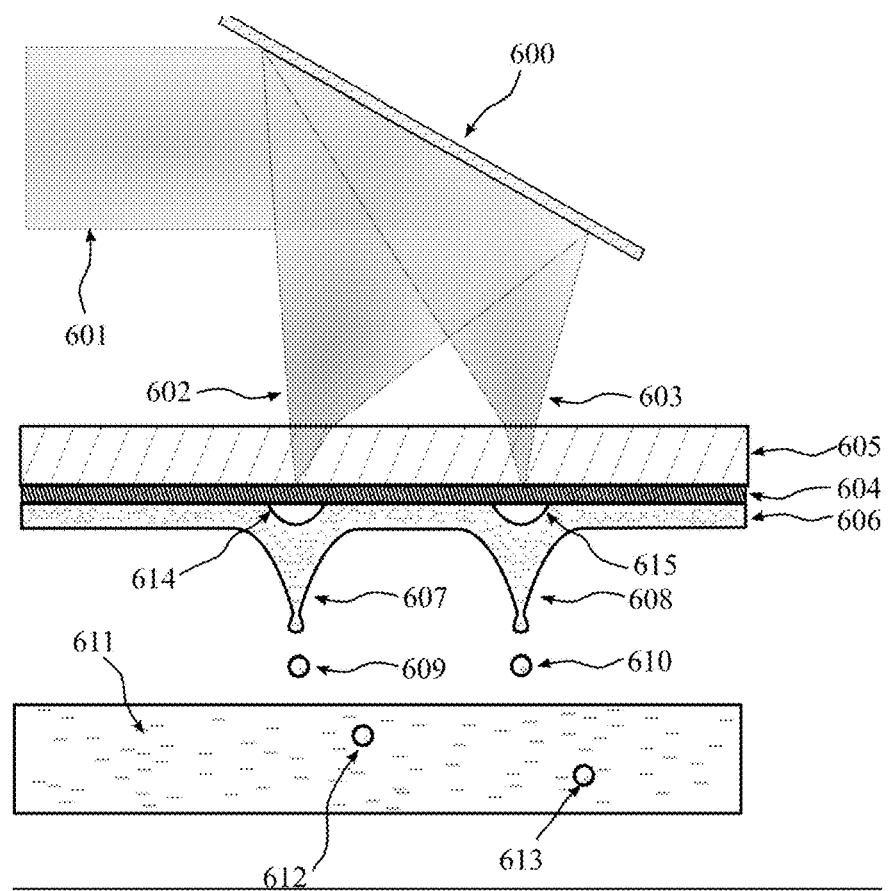
FIG. 6 shows another embodiment of the three-dimensional soft-structure printer with an optical means for simultaneous generation of multiple droplets. 600 corresponds to an optical means that can shape the incoming light beam 601 into two or more light beams 602 and 603 focused onto a thin solid-state light-absorbing film 604 which is coated onto a solid transparent support material 605, for example a beam splitter, prism lens arrangements, diffraction element, etc. The multiple light pulses 602 and 603 vaporizes parts of the thin solid-state light-absorbing film 604 and of the liquid ink 606 thus leading to the simultaneous generation of several high-velocity liquid jets 607 and 608 and the delivery of several subsequent droplets 609 and 610 into a soft supporting substrate 611. 612 and 613 correspond to droplets deposited at different depths into the soft substrate 611. 614 and 615 correspond to transient bubbles generated by the multiple light beams 602 and 603. The system shown allows for simultaneous generation of multiple droplets via light-actuation.

In at least one embodiment, the drop-on-demand system of FIG. 2 can be operated with a spatial shaping of the laser beam to simultaneously focus the laser onto several spots as described in FIG. 6. As a consequence, several droplets of different velocities are simultaneously delivered towards the soft supporting substrate, thus improving the printing speed and the throughput of the device. The laser beam shaping can be made with a digital micro-mirror device or a spatial light modulator, but not limited to.

Figure 7:
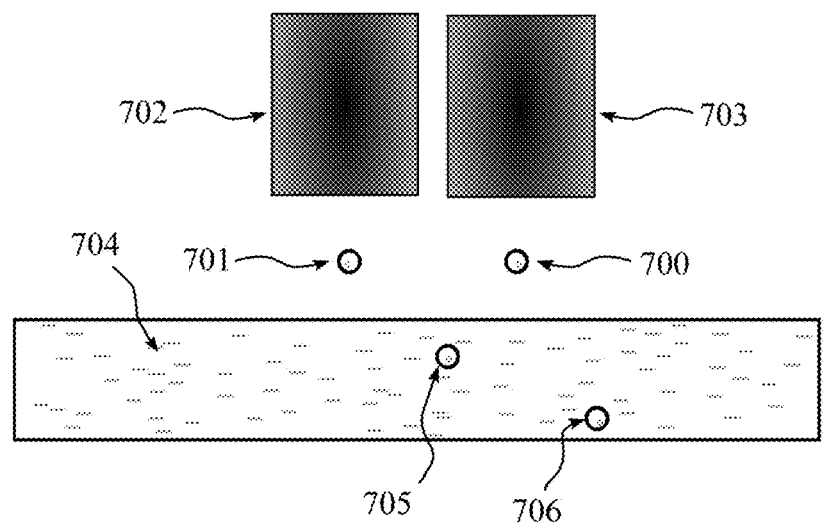
FIG. 7 another embodiment of the soft-structures printing apparatus showing two liquid droplets 700 and 701 being simultaneously ejected from two printer heads 702 and 703 towards a soft substrate 704. 705 and 706 corresponds to droplets deposited at different depths into the substrate 704. This embodiment of the system provides for simultaneous printing of multiple droplets by several printer heads.

Furthermore, in at least one embodiment of the device, the drop-on-demand system can be comprised of several inkjet printing heads simultaneously delivering droplets at different velocities as shown in FIG. 7.

Figure 8:
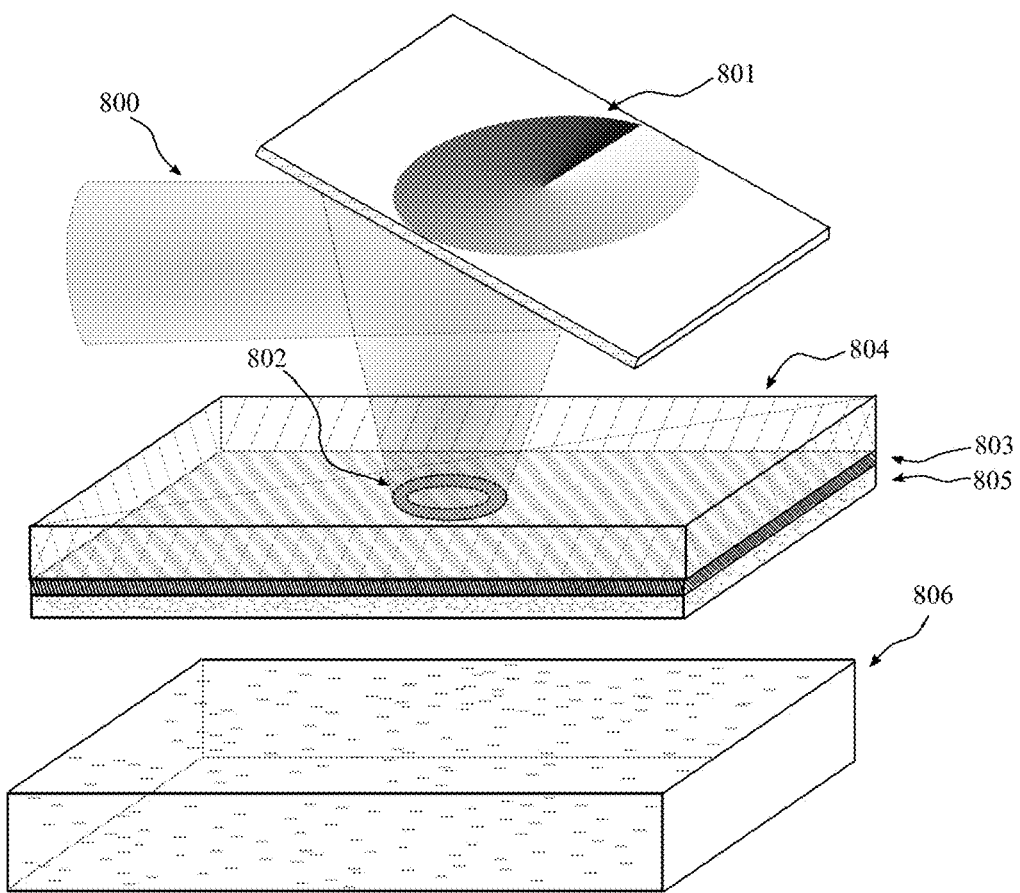
FIG. 8 shows an exemplary three-dimensional drawing of another embodiment of the soft-structures printing apparatus during light-actuation. A laser-beam 800 is spatially shaped by a phase-plate 801 to form a doughnut beam 802 focused onto a thin solid-state light-absorbing film 803 coated onto a transparent solid substrate 804. 805 corresponds to a thin layer of liquid ink coated on the solid-state light-absorbing material 803. 806 corresponds to a volume of soft substrate. This is an embodiment of the system with a spatially shaped light-actuation during actuation.
Figure 9:
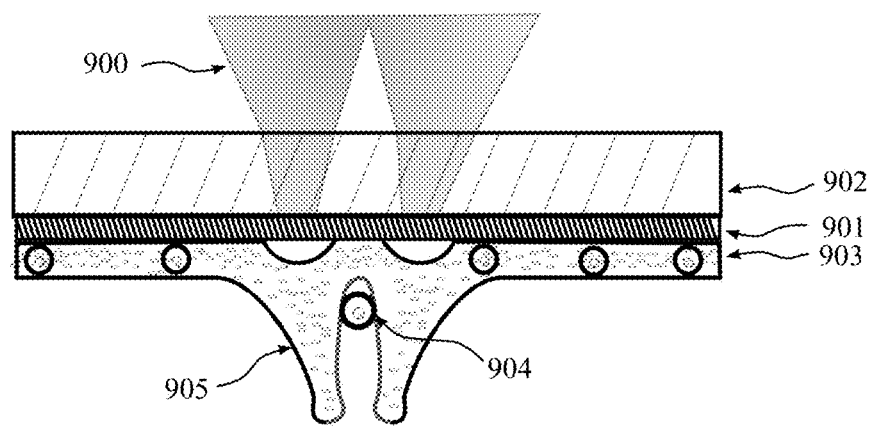
FIG. 9 shows an exemplary cross-sectional drawing of the soft-structures printing apparatus after actuation with a spatially shaped laser beam 900. The laser-beam 900 is focused onto a thin solid-state light-absorbing film 901 coated onto a transparent solid substrate 902, which leads to the vaporization of parts of the film 901 and of the liquid ink layer 903 coated on the film 901. Micro-particles 904 suspended in the liquid ink 903 are induced to flow at the front of the laser-induced jet 905 because of the spatial shaping of the laser beam (900). This is an embodiment of the system with a spatially shaped light-actuation after actuation.

In at least one embodiment, the drop-on-demand system of FIG. 2 can be operated with a spatial shaping of the laser beam to simultaneously focus the laser with a doughnut shape onto the solid-state light-absorbing film, as described in FIG. 8. Such a shape induces an annular jet that constrains the micro-particles suspended in the ink, for instance cells, to flow at the front of the induced jet, as described in FIG. 9.

Figure 10:
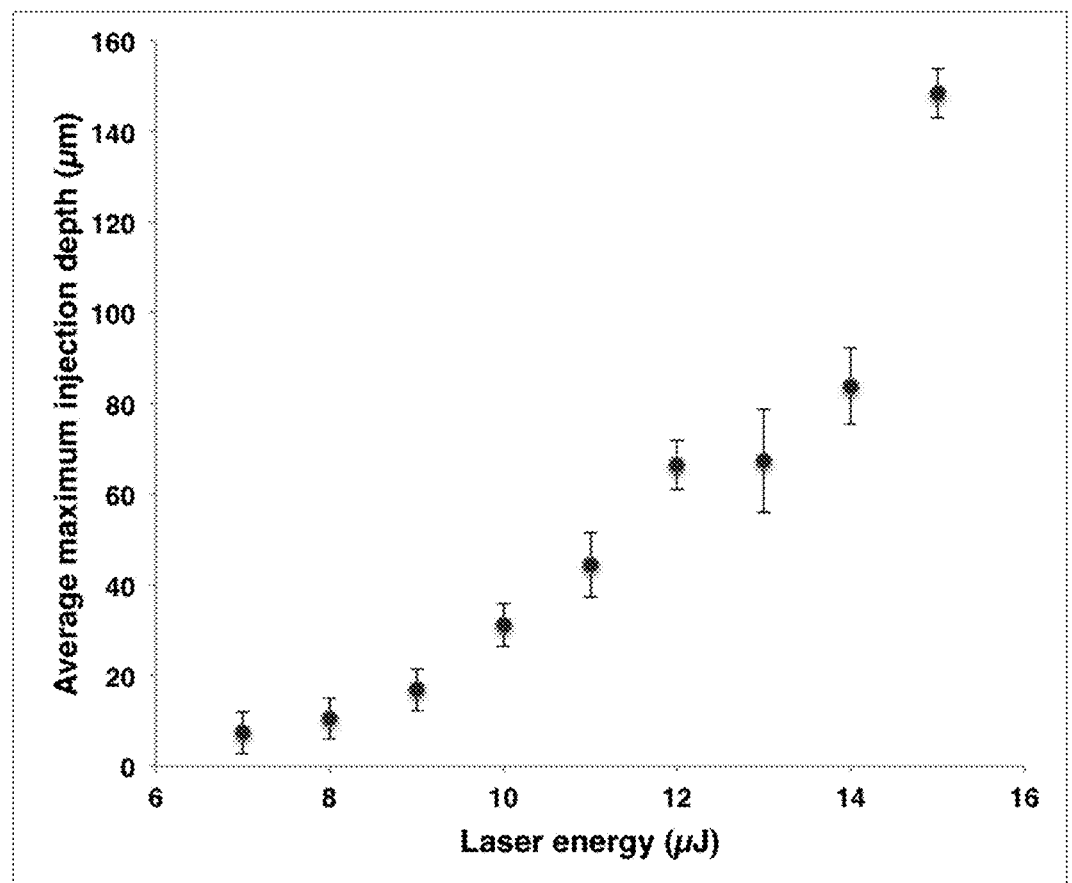
FIG. 10 depicts several samples that represent an analysis of the average injection depth of a 1% (w/v) alginate ink in water into a 2% (w/v) gelatin substrate, obtained by experiments that were performed with the exemplary device of FIG. 2. The samples show a measurement of the injection depth of an alginate-based ink into a gelatin substrate as a function of the laser energy.

As a proof of principle and to provide for experimental tests, a 1-mm thick glass microscope slides were uniformly sputtered with 60 nm of titanium. A 30-μm thick liquid layer of ink was coated on top of the titanium layer with a doctor-blade. The ink contained 30% (w/v) glycerol and 1% (w/v) alginate. By sequentially focusing an ultraviolet laser pulse of wavelength 355 nm, with a temporal width of 5 ns, and energy between 1 μJ and 15 μJ, on a spot onto the titanium film, the film was locally vaporized hence generating a transient bubble and a shockwave. When the laser energy was high enough to impart enough velocity to the liquid ink, a long thin jet was propelled towards the soft substrate, a mixture of water and 2% (w/v) gelatin of 300-g bloom force. The results demonstrate that the injection depth of the liquid ink can be controlled by varying the laser energy and therefore the jetting velocity as described in FIG. 10. As can be seen, the measured injection depth had a low standard deviation, thus indicating that the system showed good reproducibility.

Figure 11:
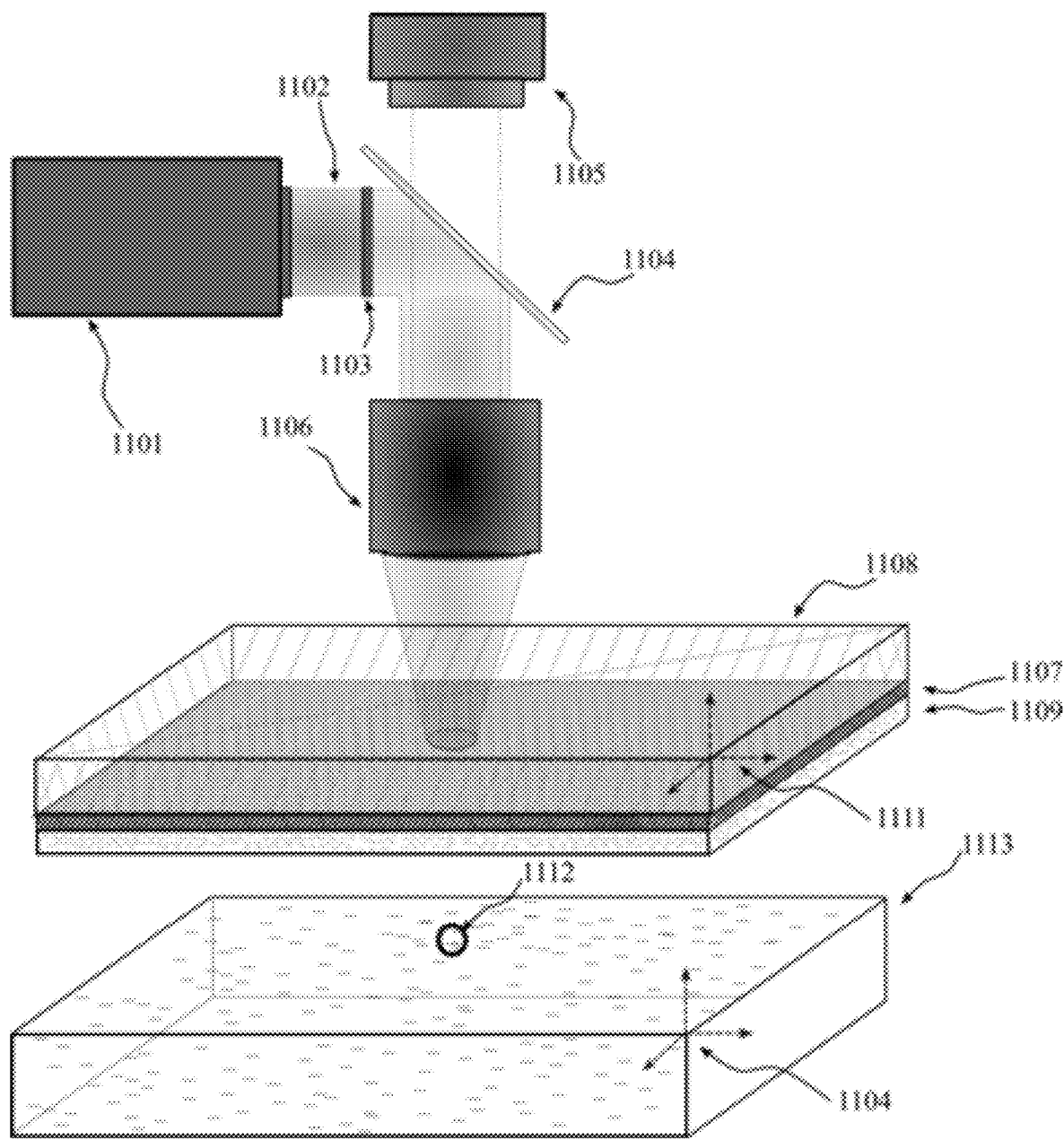
FIG. 11 schematically shows an exemplary system or a device for generating three-dimensional patterned soft structures, according to another aspect of the present invention.

FIG. 11 shows a complete schematic view of the exemplary system or device, including a laser generating light 1101, a laser beam 1102 passes through the automatized optical filter wheel 1103 allowing the control of the laser beam intensity, or other type of light intensity control device, a beam-splitter 1104 that allows simultaneous real-time camera inspection 1105 of the process, microscope objective 1106 that focuses light on the solid-state light-absorbing material 1107 coated onto a transparent solid substrate 1108. 1109 corresponds to a thin layer of liquid ink. Substrate 1108 is mounted on the motorized XYZ-stage 1111. An actuated droplet 1112 is deposited in the soft substrate bath 1113 which is placed on the motorized XYZ-stage 1114. A controller, such as a microcontroller or a data processing device is arranged to control the laser 1101 and the optical filter wheel 1103 or other type of light intensity control device to change an intensity of the laser beam that impinges on the solid-state light-absorbing material 1107, to allow for a variation of the penetration depth of the droplets.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. A method for generating a three-dimensional patterned soft structure, by using a soft supporting substrate, a drop-on-demand system with a device for varying the velocity of jetted droplets, and a liquid ink, the method comprising:
   jetting the liquid ink towards the soft supporting substrate with the drop-on-demand system;
   controlling an injection depth of the liquid ink into the soft supporting substrate by varying a jetting velocity of the liquid ink; and
   depositing droplets of the liquid ink over a volume of the soft supporting substrate to generate the three-dimensional patterned soft structure.

2. The method of claim 1, wherein the soft supporting substrate behaves as a rigid body at low shear stress and flows as a viscous liquid at higher shear stresses.

3. The method of claim 1, wherein the soft supporting substrate is a shear-thinning liquid.

4. The method of claim 1, wherein the three-dimensional patterned soft structure is based on a digital three-dimensional model.

5. The method of claim 1, wherein the liquid ink is capable of crosslinking.

6. The method of claim 1, wherein the liquid ink includes alginate.

7. The method of claim 1, wherein the soft supporting substrate includes gelatin.

8. The method of claim 1, further comprising seeding cells into the liquid ink.

9. The method of claim 1, wherein the soft supporting substrate is a reservoir of a crosslinking component of the liquid ink.

10. The method of claim 1, wherein the liquid ink droplets are deposited simultaneously.

11. The method of claim 1, wherein the liquid ink droplets are deposited serially.

12. The method of claim 1, further comprising the step of:
   depositing further liquid inks distinct from the liquid ink over the soft supporting substrate.

13. The method of claim 1, wherein the drop-on-demand system is light-actuated by a light from a light source.

14. The method of claim 13, wherein the drop-on-demand system comprises a transparent solid substrate, a thin solid-state light-absorbing film and a thin layer of the liquid ink.

15. The method of claim 13, wherein the light is simultaneously focused onto several spots.

16. The method of claim 13, wherein the light is spatially shaped and the content of a liquid jet is controlled.

17. The method of claim 1, wherein the drop-on-demand system includes an inkjet printer.

18. The method of claim 17, wherein the inkjet printer comprises several printing heads able to simultaneously generate droplets of various velocities.

19. The method of claim 1, further comprising the step of:
   printing at least one of biological tissues or organs.

20. A system for generating a three-dimensional patterned soft structure by using a soft supporting substrate, the system comprising:
- a light source for generating a light beam;
- a device for controlling an intensity of the light beam of the light source to generate a controlled light beam;
- an ink jetting layer having a liquid layer of ink, a solid-state light absorbing film, and a transparent solid layer, the controlled light beam impinging on the solid-state light absorbing film to generate a droplet from the liquid layer of ink;
- a stage for moving the controlled light beam relative to the ink jetting layer; and
- a soft supporting substrate for receiving the droplet at different penetration depths as a function of the intensity of the light beam.

* * * * *